(12) United States Patent
Nakagawa et al.

(10) Patent No.: US 7,112,428 B2
(45) Date of Patent: Sep. 26, 2006

(54) CHLOROHYDRIN AND HYDROXYCARBOXYLIC ESTER ASYMMETRIC HYDROLASE GENE

(75) Inventors: Atsushi Nakagawa, Osaka (JP); Toshio Suzuki, Osaka (JP); Atsuhiko Shinmyo, Ikoma (JP); Ko Kato, Ikoma (JP); Hideaki Idogaki, Osaka (JP)

(73) Assignee: Daiso Co., Ltd., Osaka (JP)

( * ) Notice: Subject to any disclaimer, the term of this patent is extended or adjusted under 35 U.S.C. 154(b) by 65 days.

(21) Appl. No.: 10/680,024

(22) Filed: Oct. 7, 2003

(65) Prior Publication Data

US 2004/0132154 A1    Jul. 8, 2004

(30) Foreign Application Priority Data

Oct. 7, 2002    (JP)    ............... 2002-293512

(51) Int. Cl.
*C12N 9/18* (2006.01)
*C12N 5/00* (2006.01)
*C12N 1/20* (2006.01)
C12P 21/06 (2006.01)
C12P 7/42 (2006.01)
C07H 21/04 (2006.01)

(52) U.S. Cl. ............ 435/197; 435/69.1; 435/320.1; 435/252.3; 435/252.33; 435/325; 435/146; 435/252.8; 536/23.2; 536/23.1

(58) Field of Classification Search ............ 435/252, 435/15, 193; 535/232
See application file for complete search history.

(56) References Cited

U.S. PATENT DOCUMENTS 5,543,306 A * 8/1996 Pohlenz et al. ......... 435/91.41
6,127,152 A * 10/2000 Ohta et al. .................. 435/87
6,391,597 B1   5/2002 Ohtsuka et al.
6,638,718 B1 * 10/2003 Benton et al. ............... 435/6

FOREIGN PATENT DOCUMENTS

JP    2002-171994    6/2002

OTHER PUBLICATIONS

Sang Yup Lee and Young Lee, Appl Environ Microbiol,Jun. 2003; 69(6), 3421-3426.*
Andrew Man Fai Liu, et al., Mapping the Substrate Selectivity of New Hydrolases Using Colorimetric ..., Tetrahedron: Asymmetry, vol. 12, pp. 545-556, 2001.
Sakayu Shimizu, et al., Stereoselective Reduction of Ethyl 4-Chloro-3-Oxobutanoate ..., Applied and Environmental Microbiology, pp. 2374-2377, Aug. 1990.

* cited by examiner

*Primary Examiner*—Rebecca E. Prouty
*Assistant Examiner*—Mohammad Y. Meah
(74) *Attorney, Agent, or Firm*—Lucas & Mercanti, LLP

(57) ABSTRACT

The present invention is to provide a gene having asymmetric hydrolase activity which is useful for synthesis of an optically active carboxylic acid, its antipode ester, and lactone, and a hydroxycarboxylic ester asymmetric hydrolase enzyme (EnHCH) derived from *Enterobacter sp.* DS-S-75 strain (FERM BP-5494) which is bacteria belonging to the genus *Enterobacter*, a EnHCH gene shown by base sequence of SEQ.ID.NO: 1, a gene encoding a protein having an amino acid sequence of SEQ.ID.NO: 2, and *E. coli* DH5α (pKK-EnHCH) deposited to International Patent Organism Depositary, National Institute of Advanced Industrial Science and Technology as a deposition No. FERM BP-08466.

15 Claims, 4 Drawing Sheets

CHLOROHYDRIN AND HYDROXYCARBOXYLIC ESTER ASYMMETRIC HYDROLASE GENE

BACKGROUND OF THE INVENTION

1. Field of the Invention

The present invention relates to a hydroxy carboxylic ester asymmetric hydrolase (Hydroxy Carboxylic ester Hydrolase: hereinafter abbreviated to as "EnHCH"), a gene encoding the same, a recombinant vector containing the gene, a transformant transformed by the recombinant vector and a process for producing the enzyme using the transformant, which EnHCH is a biological catalyst useful for the preparation of an optically active chlorohydrin, optically active 3-hydroxy-γ-butyrolactone, optically active hydroxycarboxylic acid, and its antipode alkyl ester which is a useful chiral building block in the synthesis of an optically active compound to be used for medicines, agricultural chemicals, and strongly dielectic liquid crystal, etc. Moreover, it relates to a process for the preparation of an optically active material using the enzyme and the transformant.

2. Prior Art

Optically active compounds have been usually produced by a chemical synthesis comprising converting the corresponding optically active starting compound into the desired compound, or by an optical resolution comprising treating the corresponding racemic compound with an optically resolving agent, but recently, it is reported to produce the optically active compound by a biological optical resolution utilizing an asymmetric reduction or asymmetric hydrolysis of a racemic compound with a microorganism or an enzyme.

As a method of preparing optically active 4-chloro-3-hydroxycarboxylic ester, E. Santaniello, et al. have reported a process for prepaing S-ethyl 4-chloro-3-hydroxybutanoate from ethyl 4-chloro-3-oxobutanoate by asymmetric reduction using baker's yeast (E. Santaniello et al., Journal of Chemical Research (J. Chem. Research), 1984, pp. 132–133). Also, Takahashi et al. have reported a process for the preparation of optically active ethyl 4-chloro-3-hydroxybutanoate from ethyl 4-chloro-3-oxobutanoate by asymmetric reduction using microorganisms (Japanese Laid-Open Patent Application No. Sho. 61-146191).

As a preparation process using an enzyme, Peters et al. have reported a process for the preparation of S-methyl 3-hydroxybutanoate and R-ethyl 4-chloro-3-hydroxybutanoate from methyl 3-oxobutanoate or ethyl 4-chloro-3-oxobutanoate by asymmetric reduction using carbonyl reductase for Rhodococcus erythropolis (J. Peters et al., Applied Microbiology Biotechnology (Appl. Microbiol. Biotechnol.), 1992, vol. 38, pp. 334–340, T. Zelinski et al., Journal of Biotechnology (J. Biotechnol.), 1994, vol. 33, pp. 283–292). Moreover, Shimizu et al. have reported a preparation process of R-ethyl 4-chloro-3-hydroxybutanoate by asymmetric reduction using aldehyde reductase for Sporoboromyces salmonicolor AKU4429 strain (Shimizu et al., Biotechnology Letter (Biotechnol. Lett.), 1990, vol. 12, pp. 593–596, Shimizu et al., Applied Microbiology Biotechnology (Appl. Microbiol. Biotechnol.), 1990, vol. 56, pp. 2374–2377).

However, in the preparation method of an optically active β-hydroxy ester compound from a prochiral β-keto ester compound by asymmetric reduction using these microorganisms or enzymes, an expensive coenzyme such as NADH (nicotinamide adenine dinucleotide) or NADPH (nicotinamide adenine dinucleotide phosphate), etc. are required for the reaction, and its oxidized product is required to be converted again into a reduced material whereby an enzyme such as glucose oxidase or formic acid dehydrogenase, etc. is separately required. Moreover, the above reaction step becomes a rate-determining reaction, and thus, the above-mentioned process cannot be said to be an industrially useful process.

As a process for the preparation of optically active 3-hydroxybutanoate, it has been known a process for the preparation of S-3-hydroxybutanoate from acetoacetate by asymmetric reduction using microorganisms such as yeast (Hamdani et al., Tetrahedron: Asymmetery, 1991, vol. 2, pp. 867–870) or Halobacterium halobium, (Ehrler and Seebach, Helvetica Chimica Acta (Helv. Chim. Acta), 1989, vol. 72, pp. 793–799). However, in this method, an expensive coenzyme such as NADH (nicotinamide adenine dinucleotide) or NADPH (nicotinamide adenine dinucleotide phosphate), etc. are required for the reaction.

When the above-mentioned Halobacterium halobium is acted on racemic 3-hydroxybutanoate, it has been reported that R-3-hydroxybutanoate remains by carboxylate hydrolysis reaction. It has been not known, however, a process for the preparation of S-3-hydroxybutanoate with high optical purity from racemic 3-hydroxybutanoate using a microorganism having a stereospecific ester resolution activity.

As a process for the preparation of optically active 2-hydroxybutanoate, it has been known a process from 2-hydroxyhexadecanoic ester or 2-hydroxytetracosanoic ester by an interesterification reaction of a secondary alcohol using lipase (Sugai et al., Yukigosei Kagakukaishi (Journal of Organic Syntesis Chemistry Association), 1995, vol. 53, pp. 48–58). However, it has been not known a process for the preparation of optically active 2-hydroxybutanoate by hydrolysis reaction of a carboxylate.

As a process for the preparation of optically active lactic acid utilizing microorganisms or enzymes, there have been known a fermentation method from glucose using lactic acid bacterium (Brin, Biochemical Preparation (Biochem. Prepn.), 1953, vol. 3, p. 61; Andersen and Greaves, Industrial Engineering Chemistry (Ind. Eng. Chem.), 1942, vol. 34, p. 34) or a preparation process from 2-halopropionic acid by a dehalogenation enzyme using a Pseudomonas genus microorganism (Soda et al., Biodegradation, 1995, vol. 6, pp. 223–227). However, it has been not known a process for the preparation of optically active lactate or lactic acid by stereospecifically hydrolyzing a carboxylate.

As a process for the preparation of optically active tetrahydrofuran-2-carboxylate by utilizing an enzyme, it has been known a process for the preparation of the same from a racemic mixture by stereospecific hydrolysis using various kinds of protease, lipase (WO 01/92553-A, WO 01/92554-A), esterase (Japanese Laid-Open Patent Application No. 2002-171994) each derived from nature. However, there is no process which can obtain R-methyl tetrahydrofuran-2-carboxylate with high optical purity. Also, the above process requires an expensive enzyme.

By the reasons as stated above, it has been strongly desired to culture a separated strain, to produce an enzyme with high properties with an inexpensive cost and a large amount whereby applying the enzyme to a process for the preparation of optically active hydroxycarboxylic acid and its antipode alkyl ester to make the process simple and ease.

Also, if a gene of the enzyme can be subjected to cloning, it is possible to produce the enzyme with an inexpensive cost and a large amount by using a genetic engineering technique, so that is has been strongly desired to subject the gene encoding the enzyme to cloning.

As a process for solving the above problems, the present inventors have already found *Enterobacter sp.* DS-S-75 strain (FERM BP-5494) separated from soil which is a bacterium belonging to the genus *Enterobacter* and having an activity of subjecting to stereoselective ester hydrolysis reaction and proposed a process for converting S-4-chloro-3-hydroxybutanoate into optically active 3-hydroxy-γ-butyrolactone by acting microorganisms or a product thereof on a chlorohydrin compound such as racemic 4-chloro-3-hydroxybutanoate to effect stereoselective dechlorination and ester hydrolysis reaction, and to recover a remaining another R-4-chloro-3-hydroxybutanoate simultaneously (see Japanese Laid-Open Patent Application No. Hei. 9-47296 and U.S. Pat. No. 5,776,766, Suzuki et al., Enzyme and Microbial Technology, 19.99, vol. 24, pp. 13–20).

They have further studied about a substrate specificity in the above-mentioned microorganism raction, and as a result, they have found that the microorganisms have characteristics of stereoselectively degrading various kinds of hydroxycarboxylic esters (Japanese Patent Application No. Hei. 13-391726). They have further studied, and as a result, they have succeeded in purifying asymmetric hydrolase (EnHCH) which participates in the above-mentioned microorganism reaction from the cells of the microorganism and in obtaining a EnHCH gene encoding the same.

SUMMARY OF THE INVENTION

The present invention is to provide a chlorohydrin and hydroxycarboxylic ester asymmetric hydrolase (EnHCH) and a gene thereof in which stereoselectivity is improved, which can markedly improve catalytic activity of a microorganism as compared with the conventional one, and can produce an optically active compound with an industrial scale by using microorganisms prepared by genetic engineering. The present invention is also to provide a vector including the gene, a transformant, and a process for producing an optically active isomer using the enzyme. The present invention is further to provide a gene which encodes a signal peptide of EnHCH which stably express gene in the transformant.

According to the present invention, it is provided a gene comprising either one of base sequences selected from:

(a) a base sequence described in SEQ.ID.NO: 1, (b) a base sequence which encodes a protein having a chlorohydrin and hydroxycarboxylic ester asymmetric hydrolase activity where the base sequence is a base sequence in which one or a plural number of base(s) is/are deleted, added or substituted from the base sequence described in SEQ.ID.NO: 1, (c) a base sequence which encodes a protein having a chlorohydrin and hydroxycarboxylic ester asymmetric hydrolase activity and hybridizes with the base sequence described in SEQ.ID.NO: 1 under stringent conditions, (d) a base sequence which encodes an amino acid sequence described in SEQ.ID.NO: 2, (e) a base sequence which encodes an amino acid sequence having a chlorohydrin and hydroxycarboxylic ester asymmetric hydrolase activity where the amino acid sequence is an amino acid sequence in which one or a plural number of amino acid(s) is/are deleted, added or substituted from the amino acid sequence described in SEQ.ID.NO: 2, and (f) a base sequence which encodes an amino acid sequence having a chlorohydrin and hydroxycarboxylic ester asymmetric hydrolase activity where the amino acid sequence is an amino acid sequence having 60% or more of homology with the amino acid sequence described in SEQ.ID.NO: 2.

Also, according to the present invention, it is provided a protein comprising either one of amino acid sequence selected from:

(a) an amino acid sequence described in SEQ.ID.NO: 2, (b) an amino acid sequence having a chlorohydrin and hydroxycarboxylic ester asymmetric hydrolase activity where the amino acid sequence is an amino acid sequence in which one or a plural number of amino acid(s) is/are deleted, added or substituted from the amino acid sequence described in SEQ.ID.NO: 2, and (c) an amino acid sequence having a chlorohydrin and hydroxycarboxylic ester asymmetric hydrolase activity where the amino acid sequence is an amino acid sequence having 60% or more of homology with the amino acid sequence described in SEQ.ID.NO: 2.

According to the present invention, it is provided a signal peptide comprising an amino acid sequence described in SEQ.ID.NO: 7 for a resting strain reaction using a transformant of the present invention.

According to the present invention, it is provided a DNA which encodes a signal peptide comprising a base sequence described in SEQ.ID.NO: 8.

According to the present invention, it is provided a vector containing the gene of the present invention. The vector preferably contains the DNA which encodes a signal peptide, and is further preferably plasmid pKK-EnHCH1.

According to the present invention, it is provided a transformant containing the above-mentioned vector. The host is preferably *E. coli*, more preferably *E. coli* JM109 strain or DH5α strain.

According to the present invention, it is provided a process for the preparation of the protein of the present invention which comprises using the gene or protein of the present invention.

According to the present invention, it is further provided a process for the preparation of an optically active compound using the protein or transformant of the present invention.

DESCRIPTION OF THE PREFERRED EMBODIMENTS

Figure 1:
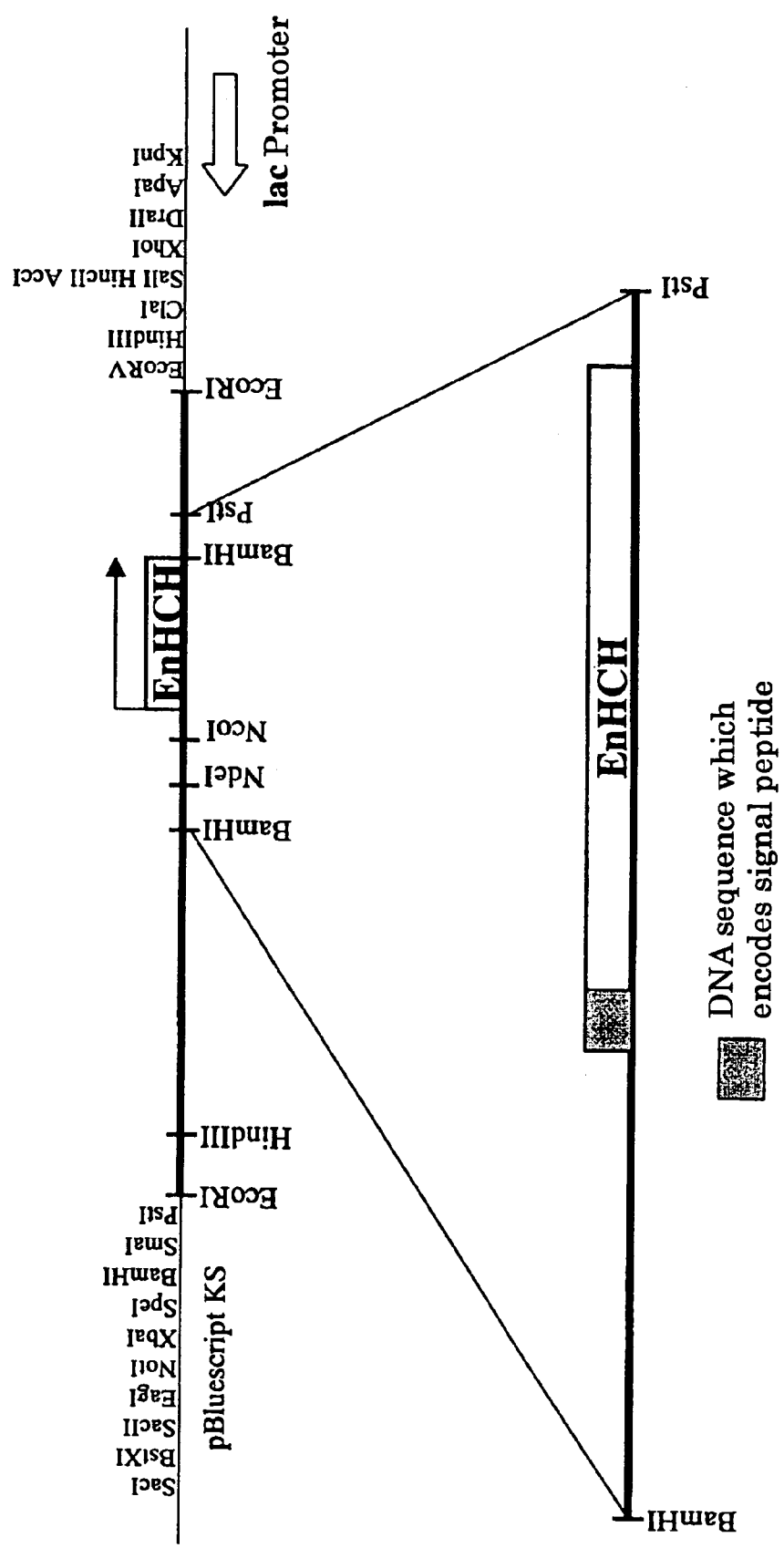
FIG. 1 is a schematic drawing showing EnHCH gene (pBl-EnHCH) which has been subjected to cloning to pBluescriptIIKS obtained by colony hybridization.

In the following, embodiments of the present invention are explained in more detail.

The present invention relates to a gene comprising either one of base sequences selected from:

(a) a base sequence described in SEQ.ID.NO: 1, (b) a base sequence which encodes a protein having a chlorohydrin and hydroxycarboxylic ester asymmetric hydrolase activity where the base sequence is a base sequence in which one or a plural number of base(s) is/are deleted, added or substituted from the base sequence described in SEQ.ID.NO: 1, (c) a base sequence which encodes a protein having a chlorohydrin and hydroxycarboxylic ester asymmetric hydrolase activity and hybridizes with the base sequence described in SEQ.ID.NO: 1 under stringent conditions, (d) a base sequence which encodes an amino acid sequence described in SEQ.ID.NO: 2, (e) a base sequence which encodes an amino acid sequence having a chlorohydrin and hydroxycarboxylic ester asymmetric hydrolase activity where the amino acid sequence is an amino acid sequence in which one or a plural number of amino acid(s) is/are deleted, added or substituted from the amino acid sequence described in SEQ.ID.NO: 2, and (f) a base sequence which encodes an amino acid sequence having a chlorohydrin and hydroxycarboxylic ester asymmetric hydrolase activity where the amino acid sequence is an amino acid sequence having 60% or more of homology with the amino acid sequence described in SEQ.ID.NO: 2.

In the present specification, the terms "one or a plural number of amino acid(s) is/are deleted, added or substituted" mean that, for example, an optional number of 1 to 20 amino acids, preferably 1 to 15 amino acids, more preferably 1 to 10 amino acids, further preferably 1 to 5 amino acids is/are deleted, added or substituted. In the present specification, the terms "one or a plural number of base(s) is/are deleted, added or substituted" mean that, for example, an optional number of 1 to 20 bases, preferably 1 to 15 bases, more preferably 1 to 10 bases, further preferably 1 to 5 bases is/are deleted, added or substituted.

In the present specification, the terms "which can hybridize under stringent conditions" mean a nucleic acid obtained by using a colony hybridization method, a plaque hybridization method, or a southern blot hybridization method, etc. which use a nucleic acid such as DNA or RNA as a probe. More specifically, there may be mentioned a DNA which is identifiable by subjecting to hybridization using a DNA derived from a colony or plaque, or a filter to which a fragment of the DNA is fixed, in the presence of 0.7 to 1.0M NaCl at 65° C., and then, washing the filter with 0.1 to 2-fold of a SSC solution (a composition of the SSC solution with a 1-fold concentration comprises 150 mM of sodium chloride and 15 mM of sodium citrate) at 65° C. The hybridization can be carried out according to the method as described in Molecular Cloning: A Laboratory Mannual, 2nd Ed., Cold Spring Harbor Laboratory, Cold Spring Harbor, N.Y., 1989. (hereinafter abbreviated to as "Molecular Cloning 2nd Ed.") and the like.

As the DNA which can hybridize under stringent conditions, there may be mentioned a DNA having homology with a certain degree or more with a base sequence of the DNA to be used as a probe, and the homology is, for example, 60% or more, preferably 70% or more, more preferably 80% or more, further preferably 90% or more, particularly preferably 95% or more, most preferably 98% or more.

In the present specification, the terms "chlorohydrin and hydroxycarboxylic ester asymmetric hydrolase" mean a protein having amino acid sequence of SEQ.ID.NO: 2 with a molecular weight of 75.0 kDa, which is a homodimer having a molecular weight of 37.5 kDa, with an isoelectric point of 6.7.

In the present specification, the terms "chlorohydrin and hydroxycarboxylic ester asymmetric hydrolase activity" mean an activity which is to subject to stereoselectively dechlorination and hydrolysis of a racemic chlorohydrin represented by the following formula [1]:

wherein $R^1$ represents a $C_1$ to $C_4$ alkyl group, to form S-3-hydroxy-γ-butyrolactone represented by the formula [2]:

and to remain R-chlorohydrin; to subject to hydrolysis stereoselectively of a racemic hydroxycarboxylic ester represented by the following formula [3]:

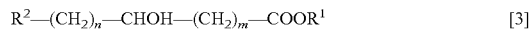

wherein $R^1$ represents a $C_1$ to $C_4$ alkyl group; $R^2$ represents a methyl group or a benzyl group; when $R^2$ is a methyl group, m is 0 and n is 0 or 1, or m is 1 and n is 0; and when $R^2$ is a benzyl group, m is 0 and n is 1;

to form an optically active hydroxycarboxylic acid and to remain its antipode ester; or to subject to hydrolysis stereoselectively of a racemic tetrahydrofuran-2-carboxylic ester represented by the following formula [4]:

wherein $R^1$ represents a $C_1$ to $C_4$ alkyl group, to remain R-tetrahydrofuran-2-carboxylic ester.

A method of obtaining a gene of the present invention is not specifically limited. An objective gene can be isolated by preparing a suitable probe or primer based on information of the base sequence of SEQ.ID.NO: 1 or the amino acid sequence of SEQ.ID.NO: 2 disclosed in the present specification, and subjecting to screening of a DNA library in which said gene is expected to be present by using the above probe or primer.

More specifically, the EnHCH gene shown in SEQ.ID.NO: 1 of the present invention can be separated from a chromosome DNA of a microorganism DS-S-75 strain (FERM BP-5494) belonging to the genus *Enterobacter*. The DNA fragment having the EnHCH gene can be obtained from the gene donor, for example, based on the partial amino acid sequence of a polypeptide chain of the purified enzyme EnHCH. That is, the purified enzyme is digested by endopeptidase, a part of the amino acid sequence of the respective fagments is determined by a protein sequencer, and a primer for the polymerase chain reaction (PCR) is synthesized based thereon. Then, PCR is carried out using a chromosome DNA of a DS-S-75 strain belonging to the genus *Enterobacter* as a template to amplify a part of the EnHCH gene whereby the base sequence is clarified. By using the obtained partial base sequence of the EnHCH gene as a probe, a DNA fragment of the objective gene can be obtained by using the hybridization method from the DNA library prepared from the chromosome DNA of the gene donor according to the conventional manner.

As a method for determining the DNA base sequence of the obtained EnHCH gene, a dideoxy sequence method may be mentioned. This method includes various kinds of methods generally used in the field of genetic engineering such as a method of amplifying a gene by PCR or a method of deleting a nucleic acid(s) by a nuclease, or the like. According to these methods, an open reading flame (ORF) which encodes whole amino acids in the objective DNA base sequence shown by SEQ.ID.NO: 1 can be confirmed.

The DNA which encodes EnHCH of the present invention is characterized in that an amino acid sequence having an EnHCH activity substantially contains a base sequence which encodes the polypeptide shown in SEQ.ID.NO: 2. Here, as long as it has an EnHCH activity, one or several number of amino acid(s) may be deleted, added or substituted in the amino acid sequence shown in SEQ.ID.NO: 2. For example, modification of DNA can be optionally carried out by the method known in the art such as a site-specific mutation introducing method using a synthetic oligonucleotide, so that some of the amino acids constituting the amino acid sequence which encodes the DNA are deleted, added or substituted. Also, by using the DNA shown in SEQ.ID.NO: 1 or a DNA which is prepared by optionally modifying the above DNA as a template, a DNA in which mutation is introduced at random can be obtained by effecting a PCR method in the presence of $Mn^{2+}$ ion (generally a concentration of 0.5 to 10 mM), or making a concentration of a specific nucleotide low. Of these DNAs thus obtained, it is needless to say that a material which encodes a protein having an EnHCH activity is included in the present invention.

Also, the present invention relates to a protein comprising either one of amino acid sequence selected from:

(a) an amino acid sequence described in SEQ.ID.NO: 2, (b) an amino acid sequence having a chlorohydrin and hydroxycarboxylic ester asymmetric hydrolase activity where the amino acid sequence is an amino acid sequence in which one or a plural number of amino acid(s) is/are deleted, added or substituted from the amino acid sequence described in SEQ.ID.NO: 2, and (c) an amino acid sequence having a chlorohydrin and hydroxycarboxylic ester asymmetric hydrolase activity where the amino acid sequence is an amino acid sequence having 60% or more of homology with the amino acid sequence described in SEQ.ID.NO: 2.

In the present specification, "an amino acid sequence having 60% or more of homology with the amino acid sequence described in SEQ.ID.NO: 2" is not specifically limited so long as it has homology with the amino acid sequence of SEQ.ID.NO: 2 of 60% or more, for example, it means 60% or more, preferably 70% or more, more preferably 80% or more, further preferably 90% or more, particularly preferably 95% or more, most preferably 98% or more.

A purification method of the enzyme according to the present invention is not specifically limited, and purification can be carried out by optionally combining purification methods generally employed in the art. For example, after crushing cells of the microorganisms by ultrasonic wave, salt out by ammonium sulfate is carried out, and a dissolved material of the precipitate is purified by optionally combining hydrophobic chromatography, anion exchange chromatography and gel filtration chromatography, until it becomes single by sodium dodecyl-sulfate-polyacrylamide gel electrophoresis (hereinafter abbreviated to as "SDS-PAGE").

The present invention also relates to a signal peptide comprising 25 amino acids shown in SEQ.ID.NO: 7 which is located at upstream of the EnHCH and a gene encoding the same (shown by SEQ.ID.NO: 8). According to this signal peptide, a transformant of E. coli into which the above gene is introduced having a high EnHCH activity can be obtained in the state of a cell culture broth. When the cell is removed, the activity is lost. It means that no enzyme is present in the medium, so that it is easy to prevent from excessive reaction or to carry out extraction of the product. Also, when necessity arises, only the gene of said signal sequence is connected to the other useful gene.

The present invention is further to provide an expression plasmid containing a base sequence of a gene which encodes an amino acid sequence showing an EnHCH activity. By incorporating a necessary portion of a DNA fragment which carries gene information of EnHCH into a vector, and it is incorporated into a host cell, a transformant can be obtained. As such a vector, preferred is a material to which a suitable selective marker, etc. which is capable of being self-replication in a host cell and is capable of selecting a recombinant host cell alone is provided, and the gene of the present invention can be expressed in a suitable host cell. Moreover, such a vector may be those which can be easily prepared from a conventionally known vector by a person skilled in the art using a conventionally known technique, or may be those which are commercially available. Particularly preferred is plasmid pKK-223-3.

The present invention is further to provide a microorganism having an ability of producing an EnHCH activity, which is transformed by a DNA which encodes the polypeptide an amino acid sequence of which is substantially shown in SEQ.ID.NO: 2.

As a host cell to be used, any material can be used without restriction so long as it is transformed by the resulting recombinant vector and can express the gene of the present inventoin. Such a host cell may include gram negative bacteria as well as gram positive bacteria so long as it can accomplish expression of the gene of the present invention along with the object of the same, and further may include either of a procaryotic cell or eucaryotic cell, or either of cells derived from animals or cells derived from plants.

As a host cell which can be used specifically in the present invention, there may be mentioned, for example, microorganisms selected from the group consisting of E. coli (Escherichia coli), the genuses Enterobacter, Saccharomyces, Xanthomonas, Acetobacter, Pseudomonas, Gluconobacter, Azotobacter, Rhizobium, Klebsiella, Salmonella and Serratia, and preferably E. coli is used. Particularly preferred is E. coli DH5α. DH5α (pKK-EnHCH1) is deposited to International Patent Organism Depositary, National Institute of Advanced Industrial Science and Technology as a deposition number FERM BP-08466.

The transformant can be obtained with a large scale by carrying out cultivation in a suitable culture medium. The culture medium may be any of usual media which contain a carbon source, a nitrogen source, inorganic substances, etc., necessary for growth of microorganisms. For example, there may be used as a carbon source, hydrocarbon such as glucose, fructose, etc., an alcohol such as glycerol, mannitol, sorbitol, propylene glycol, etc., an organic acid such as acetic acid, citric acid, malic acid, maleic acid, fumaric acid, gluconic acid and a salt thereof, or a mixture thereof. As a nitrogen source, there may be mentioned an inorganic nitrogen compound such as ammonium sulfate, ammonium nitrate, ammonium phosphate, etc., and an organic nitrogen compound such as urea, peptone, casein, yeast extract, meat extract, corn steep liquor, etc., and a mixture thereof. In addition, as an inorganic salt, phosphate, magnesium salt, potassium salt, manganese salt, iron salt, zinc salt, copper salt, etc. may be added and vitamins may be further added, if necessary. Also, as an enzyme derived additive to obtain a transformant cells having a high enzyme activity, antibiotics such as ampicillin, kanamycin, chloramphenicol, etc. may be added to a culture broth to express an objective DNA effectively depending on the strain to be used in a nutrient medium such as the above-mentioned medium, peptone medium, bouillon medium, etc., or an activation inducer of a promoter such as isopropyl β-D(−)-thiogalactopyranoside (IPTG), etc. may be used. Cultivation may be carried out under aerobic conditions by controlling an optional range at a pH of 4 to 10 and a temperature of 20 to 60° C. for 1 to 5 days, and it is more effective to carry out cultivation under optimum conditions for the transformant to be used.

Extraction of the enzyme from the resulting cells of the EnHCH-producing transformant can be carried out by the following method. According to the methods of 1) a mechanical (physical) method by French press or ultrasonic wave pulverization, 2) an enzyme treatment method such as lysozyme, 3) an autodissolution method, 4) an extraction method utilizing an osmotic pressure, etc., the transformant is broken. Also, E. coli DH5α (pKK-EnHCH1) can be utilized as a high activity enzyme in the state of a culture broth without pulverizing the cells.

The enzyme produced by the present process is not limited only to those which are accorded with the polypeptide sequence of EnHCH in the origin of the genus Enterobacter, and it may include any polypeptides obtained by gene recombinant methods such as base sequence transformation or gene transformation, and show an EnHCH activity. That is, those in which one or several number of amino acids in the peptide sequence is/are deleted, or one or several number of amino acids in the peptide sequence is/are substituted by other amino acid(s).

The thus produced transformant which produces a stereoselective hydrolase with a large amount can be prepared with an industrial scale in an inexpensive medium, and it can be utilized as a bioreactor for the preparation of R-4-chloro-3-hydroxycarboxylic ester, S-3-hydroxy-γ-butyrolactone, optically active hydroxycarboxylic acid, and its antipode ester, R-tetrahydrofuran-2-carboxylic ester, etc.

In particular, E. coli DH5α (pKK-EnHCH1) shows higher reactivity as compared with a gene donor (DS-S-75 strain of the genus Enterobacter), and it is particularly possible to obtain S-3-hydroxy-γ-butyrolactone, R-3-hydroxybutyric acid, and S-2-hydroxybutyric acid within a short period of time with a high optical purity.

EXAMPLES

In the following, the present invention is explained by referring to Examples in more detail. The present invention is not at all limited by these Examples.

Example 1

Purification of EnHCH Enzyme

Measurement of an enzyme activity was carried out by using 1% (v/v) methyl 4-chloro-3-hydroxybutanoate as a substrate and reacting in 0.5 M potassium phosphate buffer (pH 7.15) at 30° C., and liberated chloro ions were calorimetrically determined according to the method of Iwasaki et al. (Bull. Chem. Soc. Japan, 25, 226 (1952)). An enzyme amount which liberates 1 μmol of chloro ion within one minute is defined to be 1 U. Determination of the protein was carried out by measuring an absorption at 280 nm.

DS-S-75 strain (FERM BP-5494) belonging to the genus Enterobacter was cultured in a PYG medium (1% peptone, 1% yeast extract and 1% glycerol, pH 7.2), and cells were prepared by centrifugation.

The resulting wet cells were pulverized by an ultra high-pressure cell pulverizing device, and then, cell residue were removed by centrifugation to obtain cell-less extract. To the extract was added ammonium sulfate, and precipitated fraction at 50% saturation was recovered. Moreover, it was applied to hydrophobic chromatography by Butyl-toyoperl equilibrated with 10 mM tris-sulfate buffer (pH 7.8) containing 1.6 M of ammonium sulfate. A concentration of ammonium sulfate was lowered to 0 M, and an active fraction of the enzyme was recovered. To the fraction was added ammonium sulfate, and precipitates at 80% saturation were dissolved in 10 mM tris-sulfate buffer (pH 7.8), and dialyzed by the same buffer. After dialysis, the resulting material was applied to ion exchange column chromatography by DEAE-sepharose equilibrated with the same buffer. Dissolution was carried out with concentration gradient (10–200 mM) of the same buffer, and active fractions of the enzyme were recovered. These fractions were subjected to desalting concentration by using ultrafiltratoin membrane (Macrosep 10K, available from Nihon Pall Ltd.). The concentrate was applied to gel filtration column chromatography using Sephadex-G150 equibrated with 0.1 M potassium phosphate buffer, to recover active fractions of the enzyme.

The resulting asymmetric hydrolase standard product was analyzed by SDS-PAGE, and as a result, it became a single band and the molecular weight was 37.5 kDa. As results of gel filtration column chromatography and Native-PAGE using a separation gel to which 10–20% of concentration gradient had been applied, the molecular weight was 75 kDa. From these results, it counld be found that the enzyme was homo dimer of subunits having a molecular weight of 37.5 kDa.

Summary of the purification was shown in Table 1, specific activity of the purified enzyme was 7690 U/mg-protein, and was 221-fold as compared to the crude enzyme extract.

TABLE 1

| | Volume (ml) | Total protein weight (mg) | Total activity (U) | Specific activity (U/mg) | Yeild (%) | Purified degree (fold) |
|---|---|---|---|---|---|---|
| Crude extract | 90 | 2540 | 88300 | 34.8 | 100 | 1.0 |
| 0–50% ammonium sulfate precipitate | 200 | 1680 | 53800 | 32.0 | 61.0 | 0.90 |
| Butyl toyopearl | 173 | 142 | 31800 | 269 | 43.2 | 7.70 |
| 0–80% ammonium sulfate precipitate | 38.3 | 132 | 23000 | 174 | 26.0 | 5.0 |
| DEAE-sepharose | 75.3 | 5.95 | 28200 | 4750 | 32.0 | 136 |
| Sephadex G-150 | 16.8 | 2.54 | 19500 | 7690 | 22.1 | 221 |

Example 2

Analysis of Partial Amino Acid Sequence of EnHCH Enzyme

Purified EnHCH enzyme in an amount of 45 μg was treated with chymotrypsin at 37° C. for 1 hour. SDS-PAGE was carried out by using 12.5% separation gel, the resulting material was transcripted to a PVDF membrane, and N terminus and internal partial amino acid sequences were determined by an amino acid sequencer. The determined amino acid sequences are shown in SEQ.ID.NO: 3 and 4.

Example 3

Cloning of EnHCH Gene (1) Preparation of Chromosome DNA from the Genus *Enterobacter*

DS-S-75 strain (FERM BP-5494) belonging to the genus *Enterobacter* was cultured in 5 ml of a PYG medium for 20 hours, and cells were recovered by centrifugation. The cells were suspended in 490 ml of a TE solution (10 mM Tris-hydrochloride, pH 8.0, 1 mM EDTA), 30 ml 10% SDS and 50 ml of 20 mg/ml protease K were added thereto, and the mixture was reacted at 50° C. for 1 hour. Thereafter, extraction was carried out with an equal amount of phenol:chloroform:isoamyl alcohol (25:24:1), 0.1-fold amount of 3 M sodium acetate solution was added thereto, and 0.6-fold amount of 2-propanol was quietly layered. As a result, DNA generated at an interface was recovered by a glass lod by wounding it in a string state.

The obtained DNA was dissolved in 500 ml of a TE solution. About 1.1 mg of chromosomal DNA was obtained.

(2) Preparation of Probe

PCR primer having a DNA sequence expected from amino acid sequences of SEQ.ID.NO: 3 and 4 determined by an amino acid sequencer was synthesized (as shown in SEQ. ID. NO: 5 and 6) by considering codon degeneration, 40 cycles of PCR (thermal denaturation: 96° C. for 30 seconds, annealing: 50° C. for 1 minute, elongation reaction: 72° C. for 1 minute) were carried out by using ExTaq DNA polymerase (available from Takara Shuzo Co., Ltd.) and 50 ng of chromosome DNA extracted in (1) as a template, then, after cooling to 4° C., amplified DNA was confirmed by agarose gel electrophoresis, and a DNA fragment was recovered by agarose gel according to the conventional manner. Then, the DNA fragment was subjected to subcloning to pUC118 (available from Takara Shuzo Co., Ltd.), and the base sequence was determined by a DNA sequencer. As a result, in the determined DNA base sequence, a region which encodes a partial amino acid sequence (SEQ.ID.NO: 3 and 4) previously determined can be determined, so that the obtained amplified DNA was labeled by $^{32}$P according to the conventional manner to make a probe DNA.

(3) Preparation of Restriction Enzyme Map

The chromosome DNA of the extracted DS-S-75 strain was cut by various kinds of restriction enzymes, after subjecting to electrophoresis by using 1% agarose gel, it was transcripted to a nitrocellulose membrane. After air drying, hybridization reaction was carried out by using the probe prepared in (2) at 65° C. for 20 hours.

The membrane subjected to hybridization was washed with (1) 2×SSC, 65° C. for 15 minutes and (2) 1×SSC, 65° C. for 30 minutes, and autoradiogram was taken by attaching thereto an X-ray film and a sensitizing paper. As a result, by comparing various signals to each other, a restriction enzyme map at a neighbour of EnHCH gene region was prepared.

(4) Cloning of Gene from Genome Library

Genome library in which many kinds of DNA fragments derived from chromosome DNAs of about 6000 base pairs of DS-S-75 strains were inserted into EcoRI portion of plasmid pBluescriptII KS (available from TOYOBO CO., LTD.) was prepared with consideration that whole length of the objective EnHCH gene are contained from the restriction enzyme map prepared in (3). 160 kinds of transformants obtained by introducing the above into *E. coli* DH5α strain were replicated to a nitrocellulose membrane, the membrane was immerced into 0.5 N NaOH to effect lysis of bacteria, and the membrane was neutralized by immercing in 1 M Tris-hydrochloride (pH 7.5). After air drying, hybridization reaction was carried out by using the probe prepared in (2) at 65° C. for 20 hours.

The membrane subjected to hybridization was washed with (1) 2×SSC, 65° C. for 15 minutes, (2) 1×SSC, 65° C. for 30 minutes and (3) 0.5×SSC, 65° C. for 1 hour, and autoradiogram was taken by attaching thereto an X-ray film and a sensitizing paper. As a result, one transformant which provides a positive signal was obtained.

(5) Determination of Base Sequence

A plasmid was extracted from the above positive strain according to the conventional manner to obtain pBl-EnHCH.

Various kinds of insertion gene fragments were deleted from the pBl-EnHCH by exonuclease III and mung bean endonuclease, base sequences of the respective samples were determined by the dideoxy method, the obtained sequences are layerd, and base sequences were determined between BamHI-PstI. The determined base sequence and the amino acid sequence estimated from the base sequence are shown in SEQ.ID.NO: 1 of the sequence table. A schematic drawing of pBl-EnHCH is shown in FIG. 1. In FIG. 1, Determination of the base sequence was carried out between BamHI-PstI portions which sandwitches ORF. ORF encodes 1086 bp 362 amino acids. Of these, N-terminal side 25 amino acids are signal peptide.

Also, partial amino acid sequences of the purified EnHCH shown in SEQ.ID.NO: 3 and 4 existed in amino acid sequence estimated from the base sequence of the insertion DNA fragment derived from the positive strain, and the partial amino acid sequence was completely accored to each other.

Example 4

Preparation of Recombinant Plasmid

Figure 2:
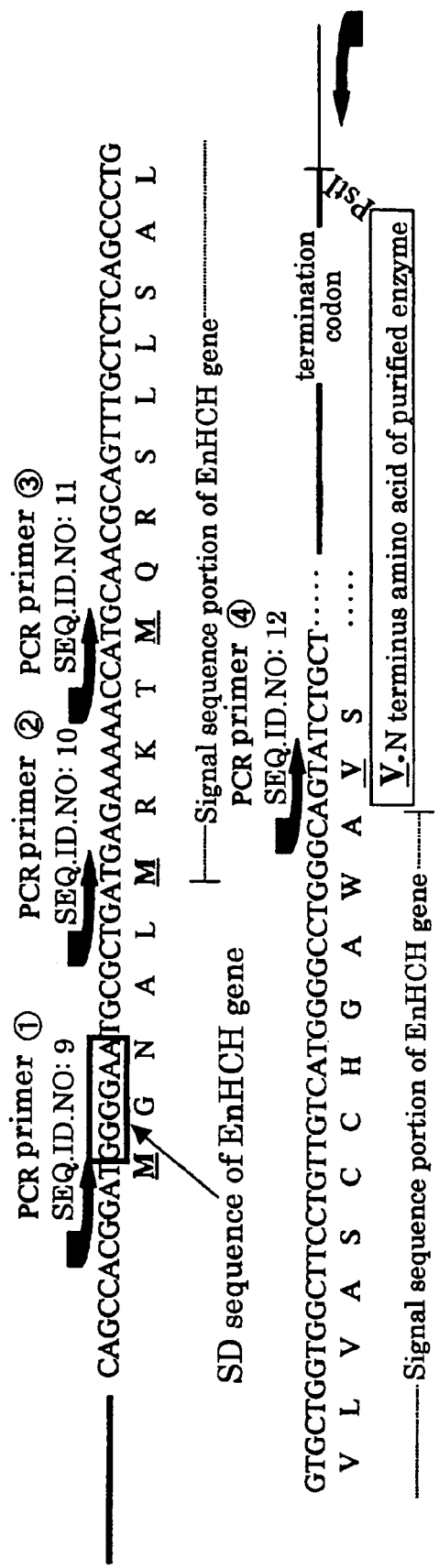
FIG. 2 is an explanation of a PCR primer for construction of pKK-EnHCH 1 to 4.
Figure 3:
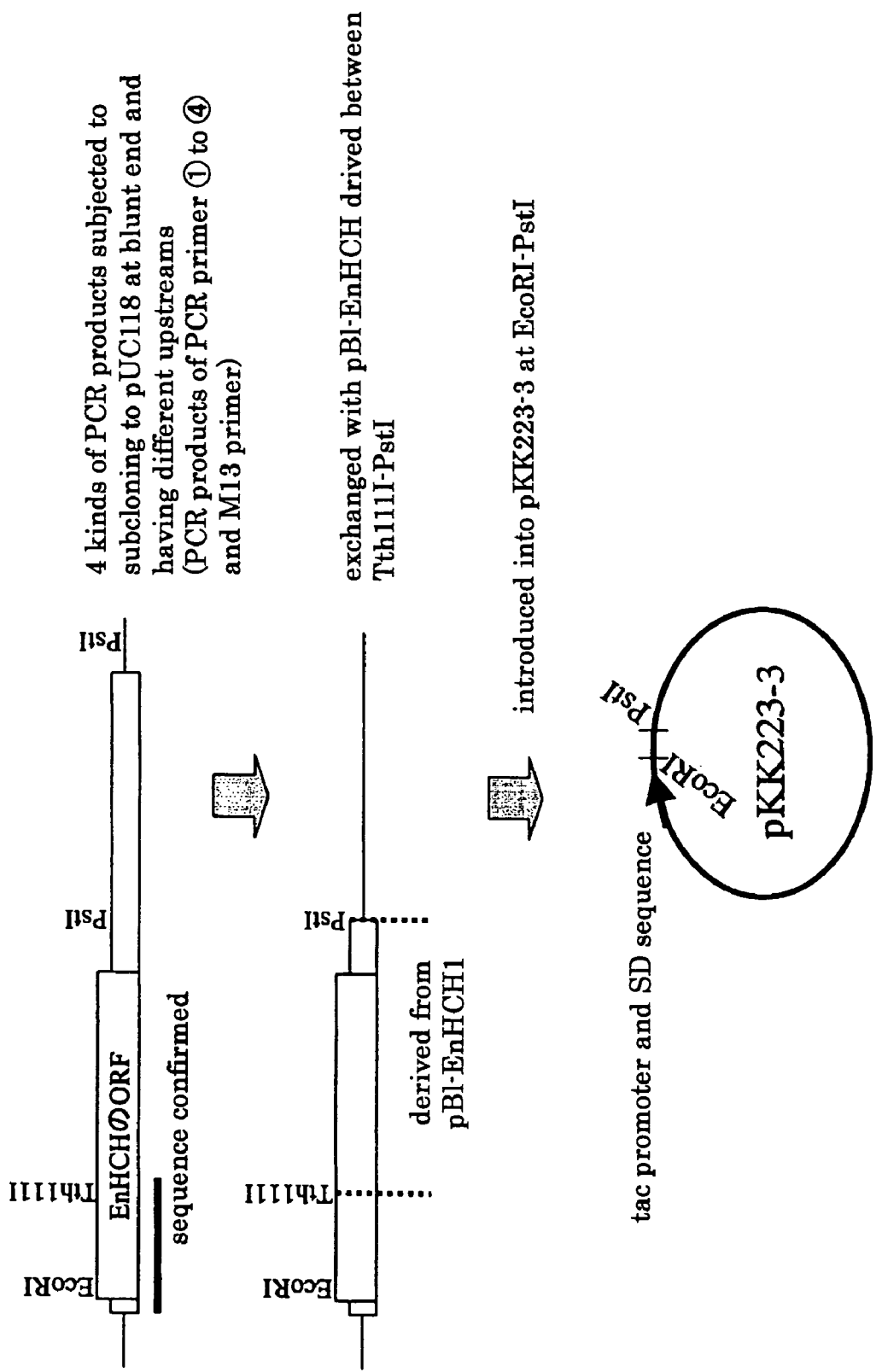
FIG. 3 shows subcloning of a PCR product obtained in FIG. 2 to a plasmid pKK223-3.

ATG sequence estimated to be an initiation codon of the EnHCH gene was present at 3 portions. Assembly was carried out by the following operation, so that coupling was carried out under control of a tac promoter of the plasmid pKK223-3 and translation was carried out from the above-mentioned respective initiation codon and N terminus of the purified enzyme (FIG. 2 and FIG. 3). To provide a EcoRI recognizable sequence to just upstream of these respective ATG sequences, PCR primers shown in SEQ.ID.NO: 9 to 12 were designed, and M13 primers were combined, 30 cycles of PCR (thermal denaturation: 96° C. for 30 seconds, annealing: 50° C. for 30 seconds, elongation reaction: 72° C. for 1 minute) was carried out by using 50 ng of pBl- EnHCH1 as a template (N terminus of the purified enzyme was substituted by methionine (FIG. 2)). In FIG. 2, with regard to three kinds of ATG sequences estimated to be initiation codons, a PCR primer in which EcoRI was added to just upstream was designed, and PCR was carried out in combination with M13 primer derived from pUC118. Also, to effect translation from valine which is the N terminus of the purified enzyme, PCR primer in which valine was substituted by methionine was designed, and PCR was carried out in the same manner. After cooling to 4° C., amplified DNA was confirmed by agarose gel electrophoresis, and various kinds of DNA fragments were recovered by agarose gel according to the conventional manner. Then, these DNA fragments were smoothened by using a BKL kit (available from Takara Shuzo Co., Ltd.) and subjected to phosphorylation, and subjected to subcloning at a HincII restriction enzyme portion of pUC118. With regard to the respective samples, about 400 bases' sequences at upstream were determined by a DNA sequencer.

The obtained four kinds of plasmids were digested by restriction enzymes Tth111I and PstI, Tth111I-PstI fragment of pBl-EnHCH was inserted according to the conventional manner, and further, EcoRI-PstI digested fragment was inserted into the same portion of the pKK223-3 (available from Pharmacia Co.) vector to obtain expression plasmids pKK-EnHCH1, pKK-EnHCH2, pKK-EnHCH3 and pKK-EnHCH4 (FIG. 3). In FIG. 3, subcloning was firstly carried out to pUC118 at smooth terminus, and about 400 bp of base sequence at upstream side were determined. After confirmation that there is no PCR elongation error, sequences between Tth111I-PstI were replaced by those of pBl-En-HCH, and ligated by EcoRI-PstI to downstream of a tac promoter of pKK223-3.

Example 5

Preparation of Recombinant *E. coli*

Competent cells of *E. coli* JM109 and DH5α were prepared, and transformed by pKK-EnHCH to obtain recombinated *E. coli* JM109 (pKK-EnHCH1) and DH5α (pKK-EnHCH1). Incidentally, no DH5α (pKK-EnHCH2) could be obtained. As control samples, JM109 (pKK-223-3) and DH5α (pKK223-3) which had been transformed only by a vector were obtained.

Example 6

Expression of EnHCH Gene in Recombinant *E. coli*

(1) Preparation of Culture Broth

The transformant obtained in Example 5 was cultured under aerobic conditions in a 5 ml of a LB medium (1% polypeptone, 0.5% yeast extract and 1% sodium chloride) placed in a test tube at 37° C. for 20 hours. As control samples, JM109 strain and DH5α strain each transformed by pKK223-3 were cultured in the same manner. Also, with regard to DS-S-75 strain belonging to the genus *Enterobacter*, it was seed cultured under aerobic conditions in a 5 ml of a PYG medium (1% polypeptone, 1% yeast extract and 1% glycerin) placed in a test tube at 30° C. for 20 hours, and cultured samples were obtained from the respective strains.

(2) Evaluation of Hydrolysis Activity of Recombinant

To 250 mM Tris sulfate buffer was added p-nitrophenyl butyrate, so that the final concentration became 0.05% (v/v), to prepare a reaction solution. To 3 ml of the reaction solution was added 20 ml of the cultured sample prepared as mentioned above, and the mixture was reacted at 30° C. and increase in absorbance at 400 nm derived from p-nitrophenol which had been formed by the hydrolysis reaction was measured. The results are shown in Table 2. Incidentally, 1 U represents a formed amount of 1 μmol of p-nitrophenol per 1 minute at 30° C. and specific activity per the prepared culture broth was calculated.

TABLE 2

| Name of strain | Specific activity (U/ml) |
|---|---|
| DS-S-75 strain belonging to the genus Enterobacter | 3.16 |
| JM109 (pKK-EnHCH1) | 12.6 |
| JM109 (pKK-EnHCH2) | 13.8 |
| JM109 (pKK-EnHCH3) | 2.76 |
| JM109 (pKK-EnHCH4) | 2.37 |
| JM109 (pKK223-3) | 0 |
| DH5α (pKK-EnHCH1) | 34.0 |
| DH5α (pKK223-3) | 0 |

As a result, *E. coli* transformed by the pKK-EnHCH had a hydrolysis activity, and activities of JM109 (pKK-EnHCH1), JM109 (pKK-EnHCH2) and DH5α (pKK-EnHCH1) had markedly improved as compared to that of DS-S-75 strain belonging to the genus *Enterobacter*. In particular, hydrolysis activity of DH5α (pKK-EnHCH1) per a culture broth was about 10.8-fold. Also, when the culture brothes of JM109 (pKK-EnHCH1) and DH5α (pKK-EnHCH1) were removed, then their activities were lost and it was found that no enzyme was present in the medium.

Among four strains of JM109 (pKK-EnHCH1), JM109 (pKK-EnHCH2), JM109 (pKK-EnHCH3) and JM109 (pKK-EnHCH4), JM109 (pKK-EnHCH2) showed the highest activity. Also, an SD (Shine Dalgarno) sequence to which ribosome is linked can be found at just upstream side of the second ATG sequence of the base sequence shown in FIG. 2, so that it is suggested that an inherent initiation codon of the EnHCH gene is to be the second ATG (SEQ.ID.NO: 1). That is, a methionine residue at the second portion of the amino acid sequence shown in FIG. 2 is the N terminus of the EnHCH to be inherently translated in the DS-S-75 strain. As a result, it is suggested that the gene comprises 1086 bp, and encodes 362 amino acids.

(3) SDS-PAGE of Recombinant Protein

Figure 4:
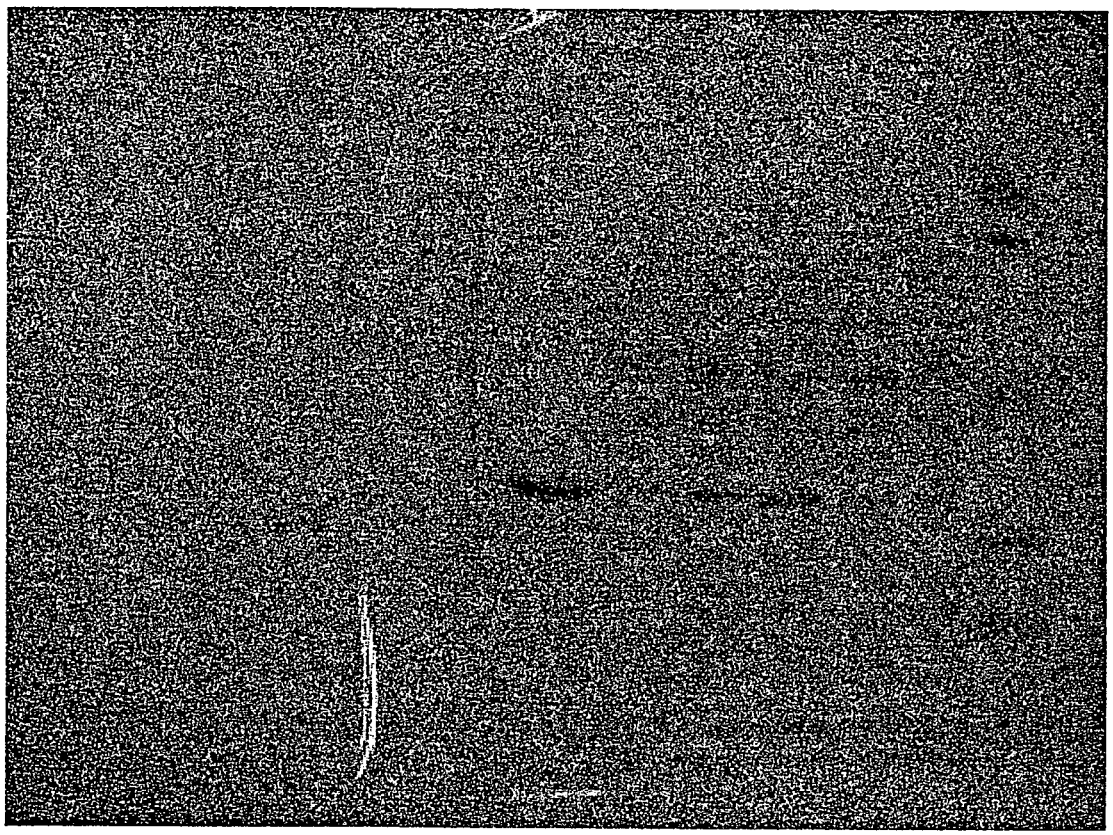
FIG. 4 is a schematic drawing of a SDS-PAGE photograph of a recombinant protein.

Cultured samples of JM109 (pKK-EnHCH1), JM109 (pKK-EnHCH2), JM109 (pKK-EnHCH3) and JM109 (pKK-EnHCH4) prepared in (1) were harvested by centrifugation, and after suspending with 20 mM potassium phosphate buffer, they were pulverized by ultrasonic wave. Each 5 μg of extracted protein samples and EnHCH purified from DS-S-75 strain belonging to *Enterobacter* were applied to SDS-PAGE (10% separation gel), and stained by Coomassie Brilliant Green. As a result, in either of recombinant enzymes of the recombinant *E. coli*, a band of the recombinant EnHCH was confirmed at the same position with that of the EnHCH purified from DS-S-75 strain belonging to *Enterobacter* (FIG. 4). Molecular weight marker to be used and the molecular weight are shown below. In FIG. 4, from the lane at the left hand, the purified EnHCH derived from the gene donor (DS-S-75 strain), an extract of JM109

(pKK223-3), an extract of JM109 (pKK-EnHCH1), an extract of JM109 (pKK-EnHCH2), an extract of JM109 (pKK-EnHCH3), an extract of JM109 (pKK-EnHCH4), molecular weight markers; Phosphorylase B (97,400), bovine serum albumin (66,200), ovoalbumin (45,000), carbonic anhydrase (31,000) and tripsin inhibitor (21,500).

As shown in Example 2, N terminus amino acid of the purified enzyme was valine. Also, at the N terminus side of the estimated amino acid sequence of the EnHCH shown by SEQ.ID.NO: 2, many hydrophobic residues, positive-charged residues and Ala-Xaa-Ala sequence as a recognized sequence to be cut are present. Thus, it is suggested that the amino acid sequence from translation initiating methionine to the $25^{th}$ residue is to be a signal peptide (SEQ.ID.NO: 7).

(4) Analysis of N Terminus Amino Acid Sequence of Recombinant EnHCH Enzyme

A sample of cell pulverized solution of JM109 (pKK-EnHCH1) prepared in (1) and precipitated by 20% to 50% ammonium sulfate was dialyzed, subjected to SDS-PAGE using 10% separation gel, transcripted to a PVDF membrane, and the N terminus sequence was determined by using an amino acid sequencer. As a result of the determination of 10 residues, they were accorded with those of the N terminus sequence of EnHCH purified from DS-S-75 strain belonging to the genus *Enterobacter*. Also, as a result of SDS-PAGE of (3), bands existed at the same positions, so that it was clarified that cleavage of the signal peptide is also done in *E. coli*. Also, activities of JM109 (pKK-EnHCH1) and JM109 (pKK-EnHCH2) are higher as compared to those of JM109 (pKK-EnHCH3) and JM109 (pKK-EnHCH4), so that the signal peptide can be said to be important for stable expression thereof in *E. coli*.

Example 7

Optical Resolution of Carboxylic Ester by Recombinant *E. coli*

(1) Optical Resolution of Methyl 4-chloro-3-hydroxybutanoate

In 300 ml volume of an Erlenmeyer flask was charged 60 ml of a LB medium containing ampicillin, and DH5α (pKK-EnHCH1) was subjected to shake culture at 37° C. for 16 hours. Also, as a control, DH5α (pKK223-3) transformed only by a vector was prepared. Moreover, DS-S-75 strain belonging to the genus *Enterobacter* was cultured in 60 ml of a PYG medium. To the respective culture brothes were added calcium carbonate and racemic methyl 4-chloro-3-hydroxybutanoate as substrates final concentrations of which became 5% (w/v) and 8% (w/v), respectively, and the mixture was reacted at 30° C. for 1 hour under shaking. Also, DS-S-75 strain belonging to the genus *Enterobacter* was further reacted for 24 hours under shaking with a substrate a final concentration of which became 2%. After completion of the reaction, the cells were removed by centrifugation, and a concentration of the methyl 4-chloro-3-hydroxybutanoate remained in the reaction mixture was analyzed by gas chromatography (column carrier: PEG20M, 60–80 mesh). Further, the above-mentioned cell-removed solution was extracted with an equal amount of ethyl acetate, and an optical purity of the methyl 4-chloro-3-hydroxybutanoate remained in the mixture was measured by gas chromatography using G-TA (0.25 mm×30 m) manufactured by ASTEC INC. As a result, a retension time was 14.7 minutes for R isomer and 15.7 minutes for S isomer. Analytical conditions: column temperature: 110° C., detector temperature: 200° C., carrier gas: nitrogen; flow rate: 0.8 ml/min, detector: FID; sprit ratio: 100/1.

Moreover, the mixture was extracted twice with ethyl acetate, and the aqueous fraction was concentrated by an evaporator. The concentrate was dehydrated by anhydrous magnesium sulfate to obtain syrup of 3-hydroxy-γ-butyrolactone. To 10 ml of syrup were added 500 ml of 1,2-dichloroethane and 100 ml of trifluoroacetic acid anhydride and the mixture was allowed to stand for 30 minutes to carry out trifluorination. The solvent was removed under reduced pressure, the residue was dissolved in ethanol, and an optical purity of the 3-hydroxy-γ-butyrolactone was measured by gas chromatography using G-TA (0.25 mm×30 m). A retension time was 18.7 minutes for R isomer and 19.9 minutes for S isomer. Analytical conditions: column temperature: 120° C., detector temperature: 200° C., carrier gas: nitrogen; flow rate: 0.8 ml/min, detector: FID; sprit ratio: 100/1.

As a result, a reaction rate of DH5α (pKK-EnHCH1) was improved as compared to that of the gene donor (DS-S-75 strain belonging to the genus *Enterobacter*). Also, it had a high stereoselectivity, and both of R-methyl 4-chloro-3-hydroxybutanoate and formed S-3-hydroxy-γ-butyrolactone had high optical purities, and almost all amount of the S-ethyl 4-chloro-3-hydroxybutanoate had been converted into S-3-hydroxy-γ-butyrolactone. Also, DH5α (pKK223-3) had no optical resolution ability. After the reaction, measured results of an optical purity of the remaining R-methyl 4-chloro-3-hydroxybutanoate, a yield thereof when an amount of the racemic methyl 4-chloro-3-hydroxybutanoate before initiation of the reaction as 100%, and an optical purity of the formed S-3-hydroxy-γ-butyrolactone are shown in Table 3.

TABLE 3

| | Methyl 4-chloro-3-hydroxybutanoate | | 3-Hydroxy-γ-butyrolactone |
|---|---|---|---|
| | Optical purity (% ee) | Yield (%) | Optical purity (% ee) |
| DH5α (pKK-EnHCH1) (1 hr) (substrate 8%) | 99.1 (R) | 49.2 | 99.9 (S) |
| DH5α (pKK-223-3) (1 hr) (substrate 8%) | 0 | 100 | Not formed |
| DS-S-75 (1 hr) (substrate 8%) | 11.8 (R) | 88.4 | N.D. |
| DS-S-75 (24 hr) (substrate 8%) | 99.5 (R) | 48.0 | 95.9 (S) |

(2) Optical Resolution of Ethyl 3-hydroxybutanoate

Various kinds of cells were cultured in the same manner as in Example 7 (1), to the respective culture brothes were added calcium carbonate and racemic ethyl 3-hydroxybutanoate as substrates final concentrations of which became 5% (w/v) and 8% (w/v), respectively, and they were reacted at 30° C. for 1 hour under shaking. Also, DS-S-75 strain belonging to the genus *Enterobacter* was further reacted for 4 hours under shaking. After completion of the reaction, the cells were removed by centrifugation.

A concentration of the ethyl 3-hydroxybutanoate remained in the reaction mixture was analyzed by gas chromatography (column carrier: PEG20M, 60–80 mesh). Further, the above-mentioned cell-removed solution was extracted twice with an equal amount of ethyl acetate, and the solvent of the ethyl acetate layers were removed under reduced pressure to obtain a syrup of ethyl 3-hydroxybutanoate. The obtained product was subjected to trifluorination by trifluoroacetic anhydride, and an optical purity thereof was measured by gas chromatography using G-TA (0.25 mm×30 m) manufactured by ASTEC INC. A retension time was 8.1 minutes for R isomer and 12.1 minutes for S isomer. Analytical conditions: column temperature: 90° C., detector temperature: 200° C., carrier gas: nitrogen; flow rate: 0.7 ml/min, detector: FID; sprit ratio: 100/1.

On the other hand, a concentration of 3-hydroxybutyric acid fractionated in the aqueous layer was also analyzed by gas chromatography (column carrier: PEG20M, 60–80 mesh). At this time, a pH of the aqueous solution was made pH 4 with phosphoric acid. The aqueous layer was concentrated by an evaporator to obtain a syrup of 3-hydroxybutyric acid. In 30 ml volume of an Erlenmeyer flask was charged 50 mg of the syrup, and under ice-cooling, to the syrup were added 122 mg of 4-dimethylaminopyridine, 10 ml of dichloromethane, 100 ml of ethanol and 115 mg of 1-ethyl-3-(3-dimethylaminopropyl)carbodiimide hydrochloride. After stirring the mixture for 10 minutes, and the mixture was further stirred at room temperature overnight under sealing. The organic layer was washed twice with 1N hydrochloric acid and placed in a dessiccator to remove the solvent to convert the 3-hydroxybutyric acid into ethyl 3-hydroxybutanoate. The resulting product was subjected to trifluorination in the same manner as mentioned above, and an optical purity thereof was measured by gas chromatography.

As a result, a reaction rate of DH5α (pKK-EnHCH1) was improved as compared to that of the gene donor (DS-S-75 strain belonging to the genus *Enterobacter*). Both strains had high stereoselectivity. Also, DH5α (pKK223-3) had no optical resolution ability. After the reaction, measured results of an optical purity of the remaining S-ethyl 3-hydroxybutanoate, a yield thereof when an amount of the racemic ethyl 3-hydroxybutanoate before initiation of the reaction as 100%, and an optical purity of the formed R-3-hydroxybutyric acid are shown in Table 4.

TABLE 4

| | Ethyl 3-hydroxy-butanoate | | 3-Hydroxy-butyric acid |
|---|---|---|---|
| | Optical purity (% ee) | Yield (%) | Optical purity (% ee) |
| DH5α (pKK-EnHCH1) (1 hr) (substrate 8%) | 99.2 (S) | 49.2 | 99.9 (R) |
| DH5α (pKK-223-3) (1 hr) (substrate 8%) | 0 | 100 | Not formed |
| DS-S-75 (1 hr) (substrate 8%) | 37.1 (R) | 72.0 | N.D. |
| DS-S-75 (4 hr) (substrate 8%) | 99.1 (R) | 49.0 | 98.2 (R) |

(3) Optical Resolution of Ethyl 2-hydroxybutanoate by Recombinant *E. coli*

The reaction was carried out in the same manner as in Example 7 (2) except for changing racemic ethyl 3-hydroxybutanoate with racemic ethyl 2-hydroxybutanoate. Provided that the reaction time was made 24 hours for the recombinant *E. coli*, and 24 and 36 hours for the DS-S-75 strain. After completion of the reaction, in the same manner as in Example 7 (2), the concentration and the optical purity were analyzed. A retension time was 7.4 minutes for R isomer and 7.8 minutes for S-isomer. Optical purity analyses conditions: column temperature: 90° C., detector temperature: 200° C., carrier gas: nitrogen; flow rate, 0.7 ml/min, detector: FID; sprit ratio: 100/1.

As a result, a reaction rate of DH5α (pKK-EnHCH1) was improved as compared to that of the gene donor (DS-S-75 strain belonging to the genus *Enterobacter*), and it had high stereoselectivity. After the reaction, measured results of an optical purity of the remaining R-ethyl 2-hydroxybutanoate, a yield thereof when an amount of the racemic ethyl 2-hydroxybutanoate before initiation of the reaction as 100%, and an optical purity of the formed S-2-hydroxybutyric acid are shown in Table 5.

TABLE 5

| | Ethyl 2-hydroxy-butanoate | | 2-Hydroxy-butyric acid |
|---|---|---|---|
| | Optical purity (% ee) | Yield (%) | Optical purity (% ee) |
| DH5α (pKK-EnHCH1) (24 hr) (substrate 8%) | 98.3 (R) | 49.0 | 98.9 (S) |
| DH5α (pKK-223-3) (24 hr) (substrate 8%) | 0 | 100 | Not formed |
| DS-S-75 (24 hr) (substrate 8%) | 77.3 (R) | 60.1 | N.D. |
| DS-S-75 (36 hr) (substrate 8%) | 99.2 (R) | 49.3 | 95.1 (S) |

(4) Optical Resolution of Methyl Tetrahydrofuran-2-carboxylate by Recombinant *E. coli*

Various kinds of cells were cultured in the same manner as in Example 7 (1), to the respective culture brothes were added calcium carbonate and racemic methyl tetrahydrofuran-2-carboxylate as substrates final concentrations of which became 5% (w/v) and 1% (w/v), respectively, and they were reacted at 30° C. for 2 hours under shaking. Also, DS-S-75 strain belonging to the genus *Enterobacter* was reacted in the same manner for 4 hours and 24 hours under shaking. After completion of the reaction, the cells were removed by centrifugation.

A concentration of methyl tetrahydrofuran-2-carboxylate remained in the reaction mixture was analyzed by gas chromatography (column carrier: PEG20M, 60–80 mesh). Further, an optical purity thereof was measured by gas chromatography using G-TA (0.25 mm×30 m) manufactured by ASTEC INC. A retension time was 8.4 minutes for R isomer and 9.5 minutes for S-isomer. Analytical conditions: column temperature: 110° C., detector temperature: 240° C., carrier gas: nitrogen; flow rate, 0.7 ml/min, detector: FID; sprit ratio: 100/1.

As a result, a reaction rate of DH5α (pKK-EnHCH1) was improved as compared to that of the gene donor (DS-S-75 strain belonging to the genus *Enterobacter*). After the reaction, measured results of an optical purity of the remaining R-methyl tetrahydrofuran-2-carboxylate, and a yield thereof when an amount of the racemic methyl tetrahydrofuran-2-carboxylate before initiation of the reaction as 100% are shown in Table 6.

TABLE 6

| | Methyl tetrahydrofuran-2-carboxylate | |
|---|---|---|
| | Optical purity (% ee) | Yield (%) |
| DH5α (pKK-EnHCH1) (2 hr) (substrate 1%) | 98.1 (R) | 39.6 |
| DH5α (pKK-223-3) (2 hr) (substrate 1%) | 0 | 95.0 |
| DS-S-75 (24 hr) (substrate 1%) | 95.7 (R) | 54.4 |
| DS-S-75 (48 hr) (substrate 1%) | 99.9 (R) | 46.8 |

(5) Optical Resolution of Ethyl Lactate by Recombinant *E. coli*

Various kinds of cells were cultured in the same manner as in Example 7 (1), to the respective culture brothes were added calcium carbonate and racemic ethyl lactate as substrates final concentrations of which became 5% (w/v) and 6% (w/v), respectively, and they were reacted at 30° C. for 24 hours under shaking. Also, DS-S-75 strain belonging to the genus *Enterobacter* was reacted in the same manner for 48 hours and 100 hours under shaking. After completion of the reaction, the cells were removed by centrifugation. A concentration of ethyl lactate remained in the reaction mixture was analyzed by gas chromatography (column carrier: PEG20M, 60–80 mesh). Further, the above-mentioned cell-removed solution was extracted twice with an equal amount of ethyl acetate in the same manner as in Example 7 (1) to obtain a syrup of ethyl lactate. The obtained product was subjected to trifluorination by trifluoroacetic anhydride, and an optical purity thereof was measured by gas chromatography using G-TA (0.25 mm×30 m) manufactured by ASTEC INC. A retension time was 10.1 minutes for R isomer and 11.8 minutes for S-isomer. Analytical conditions: column temperature: 70° C., detector temperature: 200° C., carrier gas: nitrogen; flow rate: 0.7 ml/min, detector: FID; sprit ratio: 100/1.

As a result, a reaction rate of DH5α (pKK-EnHCH1) was improved as compared to that of the gene donor (DS-S-75 strain belonging to the genus *Enterobacter*). After the reaction, measured results of an optical purity of the remaining R-ethyl lactate, and a yield thereof when an amount of the racemic ethyl lactate before initiation of the reaction as 100% are shown in Table 7.

TABLE 7

| | Ethyl lactate | |
|---|---|---|
| | Optical purity (% ee) | Yield (%) |
| DH5α (pKK-EnHCH1) (24 hr) (substrate 6%) | 98.7 (R) | 41.5 |
| DH5α (pKK-223-3) (24 hr) (substrate 6%) | 0 | 100 |
| DS-S-75 (48 hr) (substrate 6%) | 33.5 (R) | 65.2 |
| DS-S-75 (100 hr) (substrate 6%) | 98.7 (R) | 28.0 |

(6) Optical Resolution of Ethyl 4-phenyl-2-hydroxybutanoate by Recombinant *E. coli*

Various kinds of cells were cultured in the same manner as in Example 7 (1), to the respective culture brothes were added calcium carbonate and racemic 4-phenyl-ethyl 2-hydroxybutanoate as substrates final concentrations of which became 5% (w/v) and 2% (w/v), respectively, and they were reacted at 30° C. for 24 hours under shaking. Also, DS-S-75 strain belonging to the genus *Enterobacter* was reacted in the same manner for 48 hours and 100 hours under shaking. After completion of the reaction, the cells were removed by centrifugation.

A concentration of 4-phenyl-ethyl 2-hydroxybutanoate remained in the reaction mixture was analyzed by gas chromatography (column carrier: PEG20M, 60–80 mesh). Further, the above-mentioned cell-removed solution was extracted twice with an equal amount of ethyl acetate, and the solvent of the ethyl acetate layer was removed under reduced pressure to obtain a syrup of 4-phenyl-ethyl 2-hydroxybutanoate. The syrup was dissolved in ethanol, and an optical purity was analyzed by using high performance liqud chromatography CHIRAL CELL OD (25 cm×0.46 cm) manufactured by DAICEL CHEMICAL INDUSTRIES LTD. Analytical conditions: eluent: hexane:isopropanol (100:1), flow rate: 0.5 ml, column temperature: 25° C., detector: UV; 250 nm.

As a result, a reaction rate of DH5α (pKK-EnHCH1) was improved as compared to that of the gene donor (DS-S-75 strain belonging to the genus *Enterobacter*). After the reaction, measured results of an optical purity of the remaining R-4-phenyl-ethyl 2-hydroxybutanoate, and a yield thereof when an amount of the racemic ethyl lactate before initiation of the reaction as 100% are shown in Table 8.

TABLE 8

| | 4-phenyl-ethyl 2-hydroxybutanoate | |
|---|---|---|
| | Optical purity (% ee) | Yield (%) |
| DH5α (pKK-EnHCH1) (24 hr) (substrate 2%) | 98.1 (R) | 9.6 |
| DH5α (pKK-223-3) (24 hr) (substrate 2%) | 0 | 100 |
| DS-S-75 (48 hr) (substrate 2%) | 5.27 (R) | 73.3 |
| DS-S-75 (100 hr) (substrate 2%) | 98.1 (R) | 9.6 |

By using DH5α (pKK-EnHCH1), R-methyl 4-chloro-3-hydroxybutanoate, S-3-hydroxy-γ-butyrolactone, S-ethyl 3-hydroxybutanoate, R-3-hydroxybutyric acid, R-ethyl 2-hydroxybutanoate, S-2-hydroxybutyric acid, R-methyl tetrahydrofuran-2-carboxylate, R-ethyl lactate and R-ethyl 4-phenyl-2-hydroxybutanoate can be produced. And yet, they showed stereoselectivity substantially equal or more than that of the gene donor (DS-S-75 strain belonging to the genus *Enterobacter*), and the reaction rate was extremely rapid. That is, by incorporating a gene which encodes EnHCH, a recombinant *E. coli* having high stereoselective hydrolysis activity can be obtained. In particular, hydroxycarboxylic esters as shown in Example 7 (1) to (3) had extremely high stereoselectivity.

The invention claimed is:

1. An isolated gene comprising a nucleotide sequence selected from:
   (a) a nucleotide sequence described in SEQ. ID. NO: 1,
   (b) a nucleotide sequence which encodes a protein having a chlorohydrin and hydroxycarboxylic ester asymmetric hydrolase activity and hybridizes with the nucleotide sequence described in SEQ. ID. NO: 1 under stringent conditions,
   wherein the stringent conditions comprise hybridization using a DNA derived from a colony or plaque, or a filter to which a fragment of the DNA is fixed, in the presence of 0.7 to 1.0 M NaCl at 65° C., and then washing the filter with 0.1 to 2-fold of a SSC solution at 65° C.,
   (c) a nucleotide sequence which encodes an amino acid sequence described in SEQ. ID. NO: 2, and
   (d) a nucleotide sequence which encodes an amino acid sequence having a chlorohydrin and hydroxycarboxylic ester asymmetric hydrolase activity where the amino acid sequence is an amino acid sequence having 95% or more homology with the amino acid sequence described in SEQ. ID. NO: 2.

2. An isolated DNA which consists of the nucleotide sequence described in SEQ. ID. NO: 8.

3. A vector containing the gene according to claim 1.

4. A vector containing an isolated gene comprising a nucleotide sequence selected from:
   (a) a nucleotide sequence described in SEQ. ID. NO: 1,
   (b) a nucleotide sequence which encodes a protein having a chlorohydrin and hydroxycarboxylic ester asymmetric hydrolase activity and hybridizes with the nucleotide sequence described in SEQ. ID. NO: 1 under stringent conditions,
   wherein the stringent conditions comprise hybridization using a DNA derived from a colony or plaque, or a filter to which a fragment of the DNA is fixed, in the presence of 0.7 to 1.0 M NaCl at 65° C., and then washing the filter with 0.1 to 2-fold of an SSC solution at 65° C.,
   wherein said vector further contains the DNA as defined in claim 2.

5. The vector according to claim 4, wherein said vector is plasmid pKK-EnHCH1.

6. An isolated transformed cell containing the gene as defined in claim 1.

7. An isolated transformed cell containing the vector as defined in claim 5.

8. An isolated transformed cell containing the vector as defined in claim 4.

9. The transformant according to claim 6, wherein the host is *E. coil*.

10. The transformant according to claim 7, wherein the host is *E. coli*.

11. The transformant according to claim 8, wherein the host is *E. coli*.

12. The transformant according to claim 6, wherein the host is *E. coli* JM109 strain or DH5α strain.

13. The transformant according to claim 7, wherein the host is *E. coli* JM109 strain or DH5α strain.

14. The transformant according to claim 8, wherein the host is *E. coli* JM109 strain or DH5α strain.

15. A process for the preparation of a protein comprising an amino acid sequence selected from:

(a) an amino acid sequence described in SEQ. ID. NO: 2, and
(b) an amino acid sequence having a chlorohydrin and hydroxycarboxylic ester asymmetric hydrolase activity where the amino acid sequence is an amino acid sequence having 95% or more of homology with the amino acid sequence described in SEQ. ID. NO: 2, comprising culturing the isolated transformed cell of claim 6.

* * * * *

SEQUENCE LISTING

<160> NUMBER OF SEQ ID NOS: 12

<210> SEQ ID NO 1
<211> LENGTH: 1990
<212> TYPE: DNA
<213> ORGANISM: Enterobacter sp.
<220> FEATURE:
<221> NAME/KEY: CDS
<222> LOCATION: (742)..(1827)
<223> OTHER INFORMATION:

<400> SEQUENCE: 1

| | |
|---|---:|
| aagtggcctt ggcagagagg ttgcgttatt gatggcttcc gaaggggcat cggtcggtat | 60 |
| tgctgacctc agtctggcct cagccgaaga ggtggtccgg gaaatacaac tggctggcgg | 120 |
| tgaagcgatt gccgttggca tggatgtctc ggacgagcag cagactcagg cgggaaccga | 180 |
| cgcgctggtg aatcgttatg gcagtcttga tattctggta tctaatgccg ggatccagat | 240 |
| tgtcagtccc ctggatgaat acccgtttgc tgactggcgg aagatgatgg ctgttcatct | 300 |
| tgacggggca tttctgacca cccgggcagc actgaaacat atgtacaaaa acccgcaagg | 360 |
| ggggacggtc atttatattg ctctgtgca ttcccatgaa gcctcccggc tgaaggcggc | 420 |
| gtatgtgacc gccaaacatg gctgatggg gctggctaag gtggtcgcga aggagggggc | 480 |
| tgttcatcac gttcgctcgc atgtagtttg cccgggcttt gttgatacgc cgctggttaa | 540 |
| aaagcagatc cctgagcagg cccgtgagct gggtatcagc gaagaggatg tcgtcaaaaa | 600 |
| tattatgctg gcggaaaccg ttgacgggca gtttacatcg gaggcggata ttgccgaaac | 660 |
| agtacgtttt ctggtgacat ttccttccat ggcgctcacc ggacagtcaa ttacggtcag | 720 |
| ccacggatgg ggaatgcgct g atg aga aaa acc atg caa cgc agt ttg ctc | 771 |
|                                                          Met Arg Lys Thr Met Gln Arg Ser Leu Leu<br>                                                   1               5                       10 | |
| tca gcc ctg gtg ctg gtg gct tcc tgt tgt cat ggg gcc tgg gca gta<br>Ser Ala Leu Val Leu Val Ala Ser Cys Cys His Gly Ala Trp Ala Val<br>               15                     20                     25 | 819 |
| tct gct cag gta acc cgc gat acc ctc ggc aca atg gag aaa cag tat<br>Ser Ala Gln Val Thr Arg Asp Thr Leu Gly Thr Met Glu Lys Gln Tyr<br>           30                     35                     40 | 867 |
| caa cag atg tgg gag aaa gaa aat ggc ccg ctg acg ttg tcg cct ccg<br>Gln Gln Met Trp Glu Lys Glu Asn Gly Pro Leu Thr Leu Ser Pro Pro<br>          45                     50                     55 | 915 |
| gcc ccc ctg gcg acg ctg tta tca tcg cta ccc aaa aac agc aat aac<br>Ala Pro Leu Ala Thr Leu Leu Ser Ser Leu Pro Lys Asn Ser Asn Asn<br>60                       65                     70 | 963 |
| ccc gag tat aat acg ctc gac agc cgt gat gcg ttg act gcg ctg acc<br>Pro Glu Tyr Asn Thr Leu Asp Ser Arg Asp Ala Leu Thr Ala Leu Thr<br>75                     80                    85                    90 | 1011 |
| caa aag tac gtg acg gat aaa caa tcc ata gcc cga att atc aat gtg<br>Gln Lys Tyr Val Thr Asp Lys Gln Ser Ile Ala Arg Ile Ile Asn Val<br>               95                    100                  105 | 1059 |
| gat gtc gcg gtg ccg gga cga aaa att ccg gta cgg atc tac aac ccg<br>Asp Val Ala Val Pro Gly Arg Lys Ile Pro Val Arg Ile Tyr Asn Pro<br>          110                    115                   120 | 1107 |
| cat ccg gat ata gca acc ggg gtg att ttc ttc att cat ggt ggg ggg<br>His Pro Asp Ile Ala Thr Gly Val Ile Phe Phe Ile His Gly Gly Gly<br>             125                   130                  135 | 1155 |
| cat ctg agt ggt tcg gtg gat gtt tac gac ccg ata gcc cgt cat ctg<br>His Leu Ser Gly Ser Val Asp Val Tyr Asp Pro Ile Ala Arg His Leu<br>      140                    145                    150 | 1203 |

```
gcg gct gca acc ggt aat acc gtc gtg gca gtg gac tat cgg cgg gcg    1251
Ala Ala Ala Thr Gly Asn Thr Val Val Ala Val Asp Tyr Arg Arg Ala
155                 160                 165                 170 ccg gag tcc ccc tat ccg gag gga ctt cac gat gcg cgt gat gtc ctg    1299
Pro Glu Ser Pro Tyr Pro Glu Gly Leu His Asp Ala Arg Asp Val Leu
                175                 180                 185 atg cag gtt tac gct gta ctg gat cag aac cat gtt ccc tgg aaa ccg    1347
Met Gln Val Tyr Ala Val Leu Asp Gln Asn His Val Pro Trp Lys Pro
            190                 195                 200 caa ctg act ctg gcc gga gac agc gga ggt ggg gca ttc agc gcc acg    1395
Gln Leu Thr Leu Ala Gly Asp Ser Gly Gly Gly Ala Phe Ser Ala Thr
        205                 210                 215 ctt gcc ggc gat tta cag act gaa cac ccg ggc ttt atc tcc cgc ctg    1443
Leu Ala Gly Asp Leu Gln Thr Glu His Pro Gly Phe Ile Ser Arg Leu
    220                 225                 230 gag ctg att tat ccc agc ctg gat tac acg ttg tcc tgg cct tcc gct    1491
Glu Leu Ile Tyr Pro Ser Leu Asp Tyr Thr Leu Ser Trp Pro Ser Ala
235                 240                 245                 250 gat gaa aat ggg cag ggt aaa ttg ctt gat aaa agc aaa gtg gcc tgg    1539
Asp Glu Asn Gly Gln Gly Lys Leu Leu Asp Lys Ser Lys Val Ala Trp
                255                 260                 265 tac ttc agt cag tat ttt cag cat ggt gaa gac aga gcg tcg ctt tca    1587
Tyr Phe Ser Gln Tyr Phe Gln His Gly Glu Asp Arg Ala Ser Leu Ser
            270                 275                 280 ccg ttg tac aga tca gtc acg cgg gcg ttt ccg ccc aca ctt att ttt    1635
Pro Leu Tyr Arg Ser Val Thr Arg Ala Phe Pro Pro Thr Leu Ile Phe
        285                 290                 295 agt ggc ggt ctg gat cca tta cgt gat gag gat ttt gct ttt gtt gcc    1683
Ser Gly Gly Leu Asp Pro Leu Arg Asp Glu Asp Phe Ala Phe Val Ala
    300                 305                 310 cga ctg aaa agc gcc gga gtg ccg gtc agg cat atc cac ttc ccg ggg    1731
Arg Leu Lys Ser Ala Gly Val Pro Val Arg His Ile His Phe Pro Gly
315                 320                 325                 330 atg gta cat gca ttt ctg atg ctt gaa aat ctg gtg ccg cag caa act    1779
Met Val His Ala Phe Leu Met Leu Glu Asn Leu Val Pro Gln Gln Thr
                335                 340                 345 gca cag gtt tat cag gct acc gct gat ttc att gcc aca cca gcc cat    1827
Ala Gln Val Tyr Gln Ala Thr Ala Asp Phe Ile Ala Thr Pro Ala His
            350                 355                 360 taggtctgag gggcagtttc cgcaactgcc cctgtgattt cgttaacgaa ttacctgttc    1887
gtggcgtgat tgttttcat tgggacagaa acgcagcctt ttaagcctgc tgtctggtcg    1947
ctgccagcac aatttcgcgg atacagacgt tttgaggctg cag                    1990

<210> SEQ ID NO 2
<211> LENGTH: 362
<212> TYPE: PRT
<213> ORGANISM: Enterobacter sp.

<400> SEQUENCE: 2

Met Arg Lys Thr Met Gln Arg Ser Leu Leu Ser Ala Leu Val Leu Val
1               5                   10                  15

Ala Ser Cys Cys His Gly Ala Trp Ala Val Ser Ala Gln Val Thr Arg
            20                  25                  30

Asp Thr Leu Gly Thr Met Glu Lys Gln Tyr Gln Met Trp Glu Lys
        35                  40                  45

Glu Asn Gly Pro Leu Thr Leu Ser Pro Pro Ala Pro Leu Ala Thr Leu
    50                  55                  60
```

-continued

```
Leu Ser Ser Leu Pro Lys Asn Ser Asn Asn Pro Glu Tyr Asn Thr Leu
 65                  70                  75                  80

Asp Ser Arg Asp Ala Leu Thr Ala Leu Thr Gln Lys Tyr Val Thr Asp
                 85                  90                  95

Lys Gln Ser Ile Ala Arg Ile Ile Asn Val Asp Val Ala Val Pro Gly
            100                 105                 110

Arg Lys Ile Pro Val Arg Ile Tyr Asn Pro His Pro Asp Ile Ala Thr
        115                 120                 125

Gly Val Ile Phe Phe Ile His Gly Gly His Leu Ser Gly Ser Val
    130                 135                 140

Asp Val Tyr Asp Pro Ile Ala Arg His Leu Ala Ala Thr Gly Asn
145                 150                 155                 160

Thr Val Ala Val Asp Tyr Arg Arg Ala Pro Glu Ser Pro Tyr Pro
                165                 170                 175

Glu Gly Leu His Asp Ala Arg Asp Val Leu Met Gln Val Tyr Ala Val
                180                 185                 190

Leu Asp Gln Asn His Val Pro Trp Lys Pro Gln Leu Thr Leu Ala Gly
            195                 200                 205

Asp Ser Gly Gly Gly Ala Phe Ser Ala Thr Leu Ala Gly Asp Leu Gln
210                 215                 220

Thr Glu His Pro Gly Phe Ile Ser Arg Leu Glu Leu Ile Tyr Pro Ser
225                 230                 235                 240

Leu Asp Tyr Thr Leu Ser Trp Pro Ser Ala Asp Glu Asn Gly Gln Gly
                245                 250                 255

Lys Leu Leu Asp Lys Ser Lys Val Ala Trp Tyr Phe Ser Gln Tyr Phe
            260                 265                 270

Gln His Gly Glu Asp Arg Ala Ser Leu Ser Pro Leu Tyr Arg Ser Val
        275                 280                 285

Thr Arg Ala Phe Pro Pro Thr Leu Ile Phe Ser Gly Gly Leu Asp Pro
    290                 295                 300

Leu Arg Asp Glu Asp Phe Ala Phe Val Ala Arg Leu Lys Ser Ala Gly
305                 310                 315                 320

Val Pro Val Arg His Ile His Phe Pro Gly Met Val His Ala Phe Leu
                325                 330                 335

Met Leu Glu Asn Leu Val Pro Gln Gln Thr Ala Gln Val Tyr Gln Ala
            340                 345                 350

Thr Ala Asp Phe Ile Ala Thr Pro Ala His
        355                 360
```

<210> SEQ ID NO 3
<211> LENGTH: 27
<212> TYPE: PRT
<213> ORGANISM: Enterobacter sp.

<400> SEQUENCE: 3

```
Val Ser Ala Gln Val Thr Arg Asp Thr Leu Gly Thr Met Glu Lys Gln
 1               5                  10                  15

Tyr Gln Gln Met Trp Glu Lys Glu Asn Gly Pro
            20                  25
```

<210> SEQ ID NO 4
<211> LENGTH: 9
<212> TYPE: PRT
<213> ORGANISM: Enterobacter sp.

<400> SEQUENCE: 4

-continued

Arg Arg Ala Pro Glu Ser Pro Tyr Pro
1               5

<210> SEQ ID NO 5
<211> LENGTH: 21
<212> TYPE: DNA
<213> ORGANISM: Artificial
<220> FEATURE:
<223> OTHER INFORMATION: Designed primer sequence based on partial
       peptide sequence of EnHCH

<400> SEQUENCE: 5
aarcartayc arcaratgtg g                                             21

<210> SEQ ID NO 6
<211> LENGTH: 18
<212> TYPE: PRT
<213> ORGANISM: Artificial
<220> FEATURE:
<223> OTHER INFORMATION: Designed primer sequence based on partial
       peptide sequence of EnHCH

<400> SEQUENCE: 6

Arg Thr Ala Asn Gly Gly Asn Ser Trp Tyr Thr Cys Asn Gly Gly Asn
1               5                   10                  15

Gly Cys

<210> SEQ ID NO 7
<211> LENGTH: 25
<212> TYPE: PRT
<213> ORGANISM: Enterobacter sp.
<220> FEATURE:
<221> NAME/KEY: SIGNAL
<222> LOCATION: (1)..(25)
<223> OTHER INFORMATION:

<400> SEQUENCE: 7

Met Arg Lys Thr Met Gln Arg Ser Leu Leu Ser Ala Leu Val Leu Val
1               5                   10                  15

Ala Ser Cys Cys His Gly Ala Trp Ala
            20                  25

<210> SEQ ID NO 8
<211> LENGTH: 75
<212> TYPE: DNA
<213> ORGANISM: Enterobacter sp.

<400> SEQUENCE: 8
atgagaaaaa ccatgcaacg cagtttgctc tcagccctgg tgctggtggc ttcctgttgt    60
catggggcct gggca                                                    75

<210> SEQ ID NO 9
<211> LENGTH: 28
<212> TYPE: DNA
<213> ORGANISM: Artificial
<220> FEATURE:
<223> OTHER INFORMATION: Designed primer sequence for construction of
       pKK-EnHCH1

<400> SEQUENCE: 9
ccgaattcat ggggaatgcg ctgatgag                                      28

<210> SEQ ID NO 10
<211> LENGTH: 28
<212> TYPE: DNA

```
<213> ORGANISM: Artificial
<220> FEATURE:
<223> OTHER INFORMATION: Designed primer sequence for construction of
                        pKK-EnHCH2

<400> SEQUENCE: 10
ccgaattcat gagaaaaacc atgcaacg                                          28

<210> SEQ ID NO 11
<211> LENGTH: 28
<212> TYPE: DNA
<213> ORGANISM: Artificial
<220> FEATURE:
<223> OTHER INFORMATION: Designed primer sequence for construction of
                        pKK-EnHCH3

<400> SEQUENCE: 11
ccgaattcat gcaacgcagt ttgctctc                                          28

<210> SEQ ID NO 12
<211> LENGTH: 29
<212> TYPE: DNA
<213> ORGANISM: Artificial
<220> FEATURE:
<223> OTHER INFORMATION: Designed primer sequence for construction of
                        pKK-EnHCH4

<400> SEQUENCE: 12
ccgaattcat gtctgctcag gtaacccgc                                         29
```